(12) United States Patent
Zheng et al.

(10) Patent No.: US 10,526,267 B2
(45) Date of Patent: Jan. 7, 2020

(54) MULTITUBULAR REACTOR FOR LIQUID PHASE ALCOHOL DEHYDROGENATION AND METHOD FOR LIQUID PHASE ALCOHOL DEHYDROGENATION

(71) Applicant: FuZhou University, Fujian (CN)

(72) Inventors: Huidong Zheng, Fujian (CN); Suying Zhao, Fujian (CN); Jingjing Chen, Fujian (CN); Naixin Wu, Fujian (CN); Dan Wu, Fujian (CN)

(73) Assignee: FuZhou University, Fujian (CN)

( * ) Notice: Subject to any disclaimer, the term of this patent is extended or adjusted under 35 U.S.C. 154(b) by 26 days.

(21) Appl. No.: 15/743,287

(22) PCT Filed: Jun. 13, 2017

(86) PCT No.: PCT/CN2017/088112
§ 371 (c)(1),
(2) Date: Jan. 10, 2018

(87) PCT Pub. No.: WO2018/040666
PCT Pub. Date: Mar. 8, 2018

(65) Prior Publication Data
US 2019/0112249 A1    Apr. 18, 2019

(30) Foreign Application Priority Data

Aug. 27, 2016  (CN) .......................... 2016 1 0733149

(51) Int. Cl.
| | | |
|---|---|---|
| *C07C 45/29* | (2006.01) | |
| *B01J 19/00* | (2006.01) | |
| *B01J 19/24* | (2006.01) | |
| *B01J 23/652* | (2006.01) | |

(52) U.S. Cl.
CPC ............ *C07C 45/29* (2013.01); *B01J 19/2415* (2013.01); *B01J 23/6522* (2013.01); *B01J 2204/002* (2013.01); *B01J 2208/0007* (2013.01); *B01J 2208/00044* (2013.01); *B01J 2219/00245* (2013.01); *B01J 2523/17* (2013.01); *B01J 2523/27* (2013.01); *B01J 2523/55* (2013.01); *B01J 2523/67* (2013.01); *B01J 2523/72* (2013.01); *B01J 2523/845* (2013.01); *B01J 2523/847* (2013.01)

(58) Field of Classification Search
CPC ............................ C07C 45/29; B01J 19/2415
See application file for complete search history.

(56) References Cited

U.S. PATENT DOCUMENTS 5,449,848 A * 9/1995 Itoh ..................... B01J 8/009
585/430
6,139,810 A * 10/2000 Gottzmann ............. B01J 8/009
422/201

FOREIGN PATENT DOCUMENTS

GB         2068938 A  *  8/1981  ............. C07C 49/00

* cited by examiner

*Primary Examiner* — Sikarl A Witherspoon
(74) *Attorney, Agent, or Firm* — JCIPRNET

(57) ABSTRACT

The invention relates to a multitubular reactor for dehydrogenation of liquid phase alcohol dehydrogenation and a method of liquid phase alcohol dehydrogenation. Most of the alcohol dehydrogenation reaction is endothermic reaction, the reaction temperature is high and the equilibrium conversion rate is low.

17 Claims, 2 Drawing Sheets

MULTITUBULAR REACTOR FOR LIQUID PHASE ALCOHOL DEHYDROGENATION AND METHOD FOR LIQUID PHASE ALCOHOL DEHYDROGENATION

CROSS-REFERENCE TO RELATED APPLICATION

This application is a 371 of international application of PCT application serial no. PCT/CN2017/088112, filed on Jun. 13, 2017, which claims the priority benefit of China application no. 201610733149.X, filed on Aug. 27, 2016. The entirety of each of the above-mentioned patent applications is hereby incorporated by reference herein and made a part of this specification.

BACKGROUND

1. Field of the Invention

The present invention relates to a thermal coupling membrane reactor mainly applied to liquid phase dehydrogenation process of alcohols, in which under the action of selective permeability of the membrane, an endothermic dehydrogenation reaction takes place on one side of the membrane while the exothermic oxidation reaction takes place on the other side, thereby achieving the purposes of in situ heating, improving conversion rate and selectivity of the dehydrogenation reaction and energy saving.

2. Description of Related Art

The preparation of carbonyl-containing compounds from alcohols, as one of the most basic and important reactions, is widely applied in chemical production. Currently, there are two main methods for preparing carbonyl-containing compounds from alcohols, one is catalytic oxidation method in which a carbonyl-containing compound is prepared by the combined action of an oxidant and a catalyst, but this method has many side reactions and may produce toxic and harmful wastes; the other one is catalytic dehydrogenation method in which hydrogen is directly removed under the action of a catalyst, as the following reaction equation (1). Alcohol dehydrogenation is relatively easy to be implemented, with the reaction temperature lower than other dehydrogenation processes, less byproducts and high selectivity, but the conventional dehydrogenation process is generally carried out in the gas phase, with relatively high reaction temperature and relatively large heat consumption, and low equilibrium conversion rate due to reaction equilibrium and temperature limitations. Therefore, the use of liquid phase dehydrogenation method can avoid the above-mentioned disadvantages, and is a preferred method with relatively mild reaction conditions and high selectivity to target products.

(1)

In particular, the catalytic dehydrogenation process is implemented by direct dehydrogenation route and transfer dehydrogenation route. As the direct dehydrogenation route generally has a big problem of relatively low equilibrium conversion rate, the reverse hydrogenation reaction may likely take place when the reaction product aldehydes/ketones in the presence of hydrogen. In contrast, the transfer dehydrogenation route avoids such problem. In the transfer dehydrogenation method, a hydrogen acceptor is added into the reaction system, in order to consume the hydrogen generated by the dehydrogenation process. However, this method has strict requirements for catalysts, that is, catalysts are required for both the dehydrogenation process of alcohols and the hydrogenation process of hydrogen acceptors, and also the dehydrogenation and hydrogenation reactions are carried out in the same system, leading to the difficulty in setting process conditions.

It can be seen from the above discussion that a catalyst is required for alcohol dehydrogenation process and the catalyst performance may have a large impact on this reaction system. Based on the difference of states of catalysts, catalysts may be divided into homogeneous catalysts and heterogeneous catalysts. In a homogeneous catalytic system, catalysts are generally active and highly selective, but, the system needs the addition of alkali, organic solvents and other adjuvants, resulting in the corrosion to equipment and the difficulty in separation and recycling of catalysts; while a heterogeneous catalytic system avoids this problem and is environmentally friendly. In a heterogeneous catalytic system, the commonly used catalysts include noble metals of Pd, Pt, Ru and Au loaded on a support. The support including one of metal oxides, molecular sieves, carbon materials and organic polymers; or oxides of non-noble metals Cu, Mn, Ni, Co, Cr and V.

The conventional alcohol dehydrogenation process is mainly carried out in a fixed bed or fluidized bed reactor, but the generation of product hydrogen may limit forward progress of this reversible reaction. In recent years, membrane reactors are increasingly and widely used in the dehydrogenation process, and the so-called membrane reactors combines two separate processes of reaction and membrane separation, which achieves highly efficient reaction and in situ separation at the same time, integrating reaction and separation in one step. Membrane reactors, which are firstly applied to the biological reaction process having mild conditions, usually utilize organic membranes, the occurrence of inorganic membranes makes the commercial application of membrane reactors in petrochemical process possible.

Membranes used in alcohol dehydrogenation membrane reactors should be selectively permeable to hydrogen, and are divided into dense membranes and porous membranes based on the difference of materials. Dense membranes are mainly made of some noble metals, such as palladium and palladium alloys, which have almost 100% selectivity to hydrogen and usually used in production of phenols by benzene hydrogenation, hydrogenation of nitrites, dehydrogenation of hydrocarbons, steam reforming and other hydrogenation or dehydrogenation reactions, preferably in gas phase reactions, and also have relatively low permeability to hydrogen, particularly under relatively low reaction temperature conditions. Porous membranes are mainly made of silica, molecular sieves, carbon and ceramics, may have highly selective permeability to hydrogen under strict control of pore size, and are applicable to both gas phase and liquid phase reactions.

Although membrane reactors are currently applied to dehydrogenation process, they are mostly often used in dehydrogenation of hydrocarbons, steam reforming, water-gas shift reaction and other gas phase dehydrogenation processes. However, there are a few reports on alcohol liquid phase dehydrogenation. Also, in most of the cases reported, hydrogen generated by reaction permeates from the inner side to the outer side of a membrane, and then is blown off by a purging gas or vacuumized to increase the penetration rate, resulting in extra energy consumption and need of handling measures. However, there are a few reports on in situ utilization of hydrogen.

Patent application CN1164523A discloses gas phase catalytic dehydrogenation using a Pb-ceramic composite membrane reactor in which oxidation reaction of hydrogen and oxygen is carried out on one side of a permeable chamber. Although this process utilizes the hydrogen-oxygen reaction to provide heat for the dehydrogenation process, the Pb membrane serves as a catalyst for the reactions on the two sides and also serves for membrane separation, leading to high consumption of Pb membrane, which results in high cost and low permeability, and also, the difficulty in molding the Pb membrane causes difficult match between permeation rate and reaction rate, resulting in poor effect. The reaction rate on oxidation reaction side and the heating amount supplied at each point of dehydrogenation reaction are beyond the control. Further, this patent application is implemented by single tube reaction, resulting in low production efficiency in practical application.

On this basis, the patent application CN1189483A utilizes catalysts filled in the reaction chambers on the two sides of the membrane reactor, for gas phase catalytic dehydrogenation reaction and hydrogenation coupling reaction respectively, and by rational control of the ratio of catalyst usage amount to membrane area, the reaction rate and permeation rate are matched. However, in general, the temperature of dehydrogenation reaction is far higher than that of hydrogenation reaction, as a result, the matching of the temperature of dehydrogenation reaction and the temperature of hydrogenation reaction is a big challenge, and also, hydrogen permeated from dehydrogenation reaction side has a low pressure, the hydrogenation reaction is generally carried out under a relatively high pressure, as a result, the reaction on hydrogenation reaction side is hard to take place.

Overall, although the use of membrane reactors in dehydrogenation reactions has become more common in recent years, they are preferably used for gas phase dehydrogenation reactions using palladium membranes or palladium alloy membranes, and due to relatively low permeability to hydrogen, high cost and difficulty in molding, such membranes are difficult to use in liquid phase reactions; also, in most cases, hydrogen generated by dehydrogenation reactions is blown off by a purging gas or vacuumized rather than fully utilized. Even if treating hydrogen with hydrogenation reaction to implement thermal coupling, the patent application CN1189483A does not consider the dismatch of reaction conditions for hydrogenation and dehydrogenation reactions in industrial applicability, and barely discusses the control of thermal coupling process; furthermore, in terms of industrial applicability, in the case of using the recently reported single tube for dehydrogenation reactions, it is difficult to improve the yield, thereby affecting the benefits of plants.

SUMMARY

An object of the present invention is to provide a multitubular reactor for liquid phase alcohol dehydrogenation and a method for liquid phase alcohol dehydrogenation, which achieve controllable in situ heating and greatly improve the conversion rate of dehydrogenation reaction.

In order to achieve the object, the present invention adopts the following technical solutions:

The multitubular reactor for liquid phase alcohol dehydrogenation of the invention includes a reactor shell and a plurality of tubes spaced within the reactor shell, the tubes are made from a gas selectively permeable membrane, and the gas selectively permeable membrane is permeable to hydrogen and oxygen but impermeable to liquid molecules. A dehydrogenation catalyst is provided inside the tubes, and an oxidation catalyst is provided outside the tubes in the reactor shell. A liquid phase alcohol inlet is arranged at one end of the tubes, and a dehydrogenation product outlet is arranged at the other end of the tubes. At least one oxygen membrane tube is provided in the reactor shell. One end of the one oxygen membrane tube is an oxygen inlet, and the other end of the one oxygen membrane tube is closed. An oxidation product outlet is provided on the reactor shell.

The method for liquid phase alcohol dehydrogenation of the invention is as follows: alcohol dehydrogenation reaction and hydrogen oxidation reaction are respectively carried out on the inner side and outer side of the membrane of each tube. On the dehydrogenation reaction side, an alcohol itself or an alcohol dissolved in a solvent (in the case that the alcohol is in the solid state at room temperature) is fed into a preheater for preheating until reaching a certain temperature, and then fed through the liquid phase alcohol inlet of the tubes into the dehydrogenation side filled with a dehydrogenation catalyst for reaction. A target product is obtained from the dehydrogenation product outlet of the tubes and transported to a product region. Hydrogen generated by dehydrogenation reaction permeates the hydrogen selectively permeable membrane and enters into the reactor shell, where a catalyst for oxidation reaction is filled, oxygen is fed at a preset amount into several dedicated membrane tubes among the tubes, permeates the selectively permeable membrane and enters the oxidation side for oxidation reaction with hydrogen, and product water and excessive hydrogen are collected from the oxidation product outlet of the reactor shell.

For some alcohol raw materials in need of dissolution (alcohols are in the solid state at room temperature), a solvent required includes one of benzene solvents, such as benzene, toluene, xylene, and p-cymene, which ensures normal operation of dehydrogenation reaction of the alcohols in the liquid phase state, and such solvent is inactive to dehydrogenation reaction under the action of dehydrogenation catalysts.

The membrane used in the membrane reactor is a multitubular membrane assembly, dehydrogenation reaction and oxidation reaction take place respectively on the tube pass and shell side of each membrane tube, and the dehydrogenation catalyst and oxidation catalyst are filled in the corresponding positions.

The catalyst for dehydrogenation reaction includes noble metals Pd, Pt, Ru and Au loaded on a support, the support including one of metal oxides, molecular sieves, carbon materials and organic polymers; or one of oxides of non-noble metals Cu, Mn, Ni, Co, Cr and V, or a combination thereof; and the catalysts used are filled in the faun of particles in the reaction tubes.

As dehydrogenation is implemented by liquid phase reaction, and hydrogen generated and another feed of oxygen are both in the gas phase, it is easy to select a highly permeable and highly selective membrane. The hydrogen-oxygen gas selectively permeable membrane is made of a molecular sieve, silica, carbon, ceramics, porous stainless steel or a composite formed by two or more thereof, and the selectively permeable membrane is permeable to both hydrogen and oxygen and impermeable to liquid molecules.

The number of several oxygen dedicated membrane tubes among the tubes may be one or more than one, and they are made of a different material and may have different radius, as compared with other hydrogen selective membrane tubes. The position of the dedicated membrane tubes in the tubes is selected such that the oxidation side heating value is matched with the dehydrogenation side endothermic value at each point within the reactor. Further, this method solves the problem that hydrogen easily reaches the explosion limit on the oxidation side.

The oxidation reaction is a gas phase reaction between hydrogen and oxygen to produce water, and the catalyst used is metal platinum loaded on one of porous matrix, such as a metal oxide, a molecular sieve, a carbon material and hydrotalcite. In order to well control the reaction rate of hydrogen oxidation reaction at each point within the reactor, during the catalyst preparation, the number of active sites is controlled by controlling the loading amount of metal platinum or partially filling an inert support material, thereby providing the desired catalyst activity.

By means of catalytic oxidation, the temperature of hydrogen oxidation reaction is 50-100° C. higher than that of hydrogenation reaction, thereby maintaining the driving force for heat transfer; the amount of oxygen fed into the membrane tubes is controlled and the activity of oxidation catalyst is regulated, so as to ensure matching between the heating amount on the oxidation reaction side and the reaction heat required on the dehydrogenation reaction side, thereby achieving in situ heating. Taking cyclohexanol dehydrogenation and hydrogen oxidation as an example, the reaction heat is given as follows:

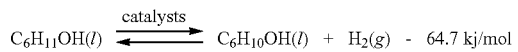

(2)

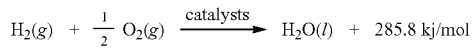

(3)

From equations (2) and (3), it can be seen that the heat generated by oxidation of 1 mol hydrogen is far more than the heat required for producing 1 mol hydrogen by alcohol dehydrogenation, therefore, the amount of heat supply from the oxidation side to the dehydrogenation side can be regulated by controlling the feed amount of oxygen to the oxidation side.

The feed stock preheating temperature of the liquid phase dehydrogenation reaction ranges from 100° C. to 450° C., the temperature of the reaction ranges from 150° C. to 500° C., and the pressure ranges from 0.1 MPa to 5 MPa.

As compared to the prior art, the present application has the following advantages:

1. Instead of adopting the oxygen feeding method provided in patent application CN1164523A, the present application adopts the method of feeding oxygen via the selective membrane tubes, which is advantageous in that oxygen permeates to the oxidation side more uniformly, and also, different amounts or activities (implemented by preparing different platinum loading amounts) of oxidation catalysts are filled in different positions to avoid the problem of failure in controlling the heating amount in each position within the reactor, thereby achieving good matching between heating amount and heat absorption amount at each point within the reactor; further, the use of this method for oxygen feeding solves the problem that hydrogen easily reaches the explosion limit on the oxidation side.

2. As dehydrogenation is implemented by liquid phase reaction and hydrogen generated and another feed of oxygen are both in the gas phase, the membrane material is selected from a variety of ranges, and easy to have high permeability and high selectivity. The membrane used in the invention is preferably a porous inorganic membrane. At present studies, palladium membranes are generally used for gas phase catalytic processes, bringing about the problems of poor permeability, high cost and difficulty in molding, however, owing to the rational design of pore size, porous inorganic membranes can achieve good selective permeability to hydrogen and oxygen, with relatively low industrial manufacturing cost and convenience in molding.

3. Most of alcohol dehydrogenation reactions are reversible, with relatively low equilibrium conversion rate. Based on the principle of reversible reaction, the forward progress of dehydrogenation reactions can be accelerated after removing the product hydrogen, therefore, the conversion rate of dehydrogenation reactions can be improved by removing the product hydrogen using the hydrogen selectively permeable membrane, thereby improving the yield of carbonyl-containing compounds; the removal of hydrogen upon reaction on the oxidation side is favorable to reduce the hydrogen partial pressure and improve the driving force for inner-membrane hydrogen permeability.

4. In the alcohol dehydrogenation reaction using the membrane reactor, the heat required for this reaction is supplied by hydrogen on the oxidation side, which has a low temperature and is convenient to control as compared to combustion, and also, since the heat generated by hydrogen oxidation is far more than the endothermic heat for dehydrogenation, the heat required for dehydrogenation reaction is supplied by controlling the addition amount of oxygen on the oxidation side and changing the activity of the catalyst in industry, thereby ensuring in situ heating and reducing energy consumption; furthermore, the product on the oxidation side is the mixture of hydrogen and water, and after simple operation of water removal, hydrogen can be recycled for other processes.

5. Different catalysts are respectively used on the two sides of the membrane to ensure the rate and selectivity of dehydrogenation reaction, as a result, as compared to the use of membranes having catalytic effect, this method can better control the progress of dehydrogenation reaction; also, the liquid phase dehydrogenation reaction and the gas phase oxidation reaction take place on the inner side and outer side of the membrane of the reactor, respectively, which is more easy to implement in industry.

6. The membrane used in the dehydrogenation reaction membrane reactor is a multitubular membrane assembly which, in terms of industrial applicability, has higher production efficiency and a more compact structure as compared to the single tube membrane reactor, and which integrates double functions, that is, serving as a reactor, and a heat exchanger for dehydrogenation reaction and oxidation reaction.

DESCRIPTION OF THE EMBODIMENTS

Figure 1:
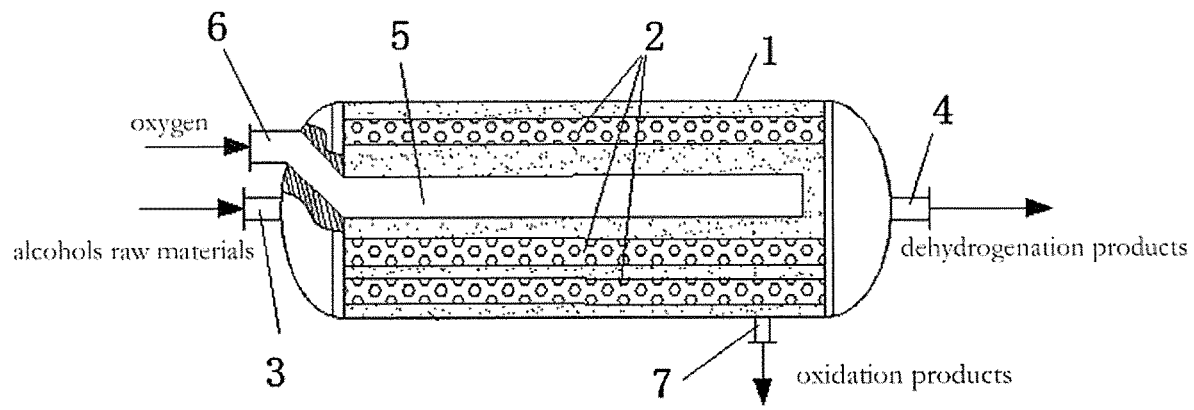
FIG. 1 is a structural schematic view of a multitubular membrane reactor of the invention.
Figure 2:
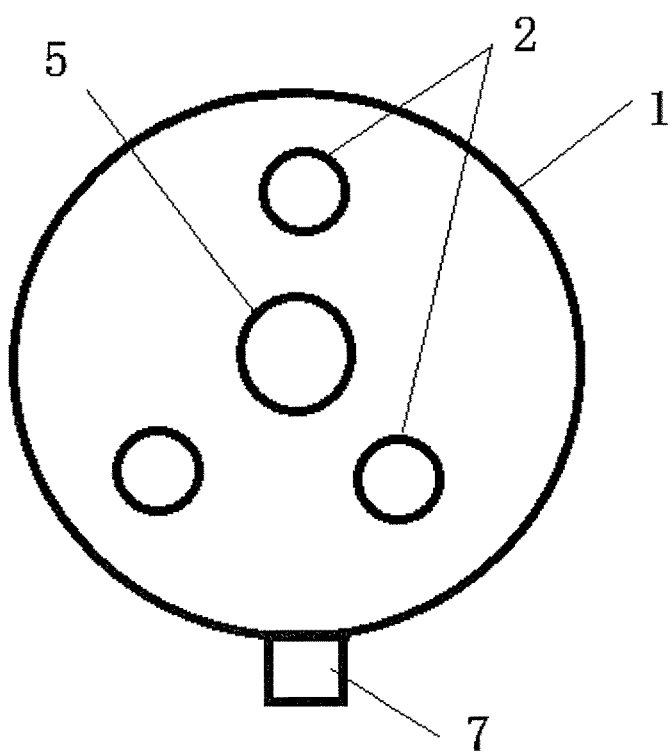
FIG. 2 is a cross-sectional view of FIG. 1.

In order to illustrate in detail, the technical solutions, structural features, objects and effects of the present invention, embodiments are described in detail in connection with the accompanying drawings.

The multitubular reactor for liquid phase alcohol dehydrogenation and a using method thereof according to the present invention are given as follows:

The multitubular reactor for liquid phase alcohol dehydrogenation of the invention includes a reactor shell 1 and a plurality of tubes 2 spaced within the reactor shell. The tubes 2 are made of a gas selectively permeable membrane, and the gas selectively permeable membrane is permeable to hydrogen and oxygen but impermeable to liquid molecules. A dehydrogenation catalyst is provided inside the tubes, and an oxidation catalyst is provided outside the tubes and located in the reactor shell. A liquid phase alcohol inlet 3 is arranged at one end of the tubes, and a dehydrogenation product outlet 4 is arranged at the other end of the tubes. One or more oxygen membrane tubes 5 are provided in the reactor shell. One end of the one oxygen membrane tube 5 is an oxygen inlet, and the other end of the one oxygen membrane tube is closed. An oxidation product outlet 7 is provided at the bottom of the reactor shell.

The method for liquid phase alcohol dehydrogenation of the present invention is as follows: alcohol dehydrogenation reaction and hydrogen oxidation reaction take place on the inner side and outer side of the membrane of the tubes 2, respectively. On the dehydrogenation reaction side, an alcohol itself or an alcohol dissolved in a solvent (in the case that the alcohol is in the solid state at room temperature) is fed into a preheater for preheating until reaching a certain temperature, and then fed through the liquid phase alcohol inlet 3 of the tubes 2 into the dehydrogenation side filled with a dehydrogenation catalyst for reaction, and a target product is obtained from the dehydrogenation product outlet 4 and transported to a product region. Hydrogen generated by dehydrogenation reaction permeates the hydrogen selectively permeable membrane and enters into the reactor shell 1, where a catalyst for oxidation reaction is filled. Oxygen is fed at a preset amount from the inlet 6 into several dedicated membrane tubes 5 among the tubes, permeates the selectively permeable membrane and enters into the reactor shell 1 for oxidation reaction with hydrogen, and product water and excessive hydrogen are collected from the oxidation product outlet 7 of the reactor shell 1.

For some alcohol raw materials in need of dissolution (alcohols are in the solid state at room temperature), a solvent required for them includes one of benzene solvents, such as benzene, toluene, xylene, and p-cymene, which ensures normal operation of dehydrogenation reaction of the alcohols in the liquid phase state, and such solvent is inactive to dehydrogenation reaction under the action of dehydrogenation catalysts.

The membrane used in the membrane reactor is a multitubular membrane assembly, dehydrogenation reaction and oxidation reaction take place respectively in the tube pass and shell side of each membrane tube, and a dehydrogenation catalyst and oxidation catalyst are filled in the corresponding positions.

The catalyst for dehydrogenation reaction includes noble metals Pd, Pt, Ru and Au loaded on a support. The support including one of metal oxides, molecular sieves, carbon materials and organic polymers; or one of oxides of non-noble metals Cu, Mn, Ni, Co, Cr and V, or a combination thereof. The catalysts used are filled in the form of particles in the reaction tubes.

As dehydrogenation is implemented by liquid phase reaction, and hydrogen generated and another feed of oxygen are both in the gas phase, it is easy to select a highly permeable and highly selective membrane. The hydrogen-oxygen gas selectively permeable membrane is made of a molecular sieve, silica, carbon, ceramics, porous stainless steel or a composite formed by two or more thereof, and the selectively permeable membrane is permeable to both hydrogen and oxygen and impermeable to liquid molecules.

The number of several oxygen dedicated membrane tubes among the tubes may be one or more than one, they are made of a different material and may have different radius, as compared with other hydrogen selective membrane tubes. The position of the dedicated membrane tubes in the tubes is selected such that the oxidation side heating value is matched with the dehydrogenation side endothermic value at each point within the reactor. Further, the use of this method solves the problem that hydrogen easily reaches the explosion limit on the oxidation side.

The oxidation reaction is a gas phase reaction between hydrogen and oxygen to produce water, and the catalyst used is metal platinum loaded on one of porous media, such as a metal oxide, a molecular sieve, a carbon material and hydrotalcite. In order to well control the reaction rate of hydrogen oxidation reaction at each point within the reactor, during the catalyst preparation, the number of active sites is controlled by controlling the loading amount of metal platinum or partially filling an inert support material, thereby providing the desired catalyst activity.

By means of catalytic oxidation, the temperature of hydrogen oxidation reaction is 50-100° C. higher than that of hydrogenation reaction, thereby maintaining the driving force for heat transfer. The amount of oxygen fed into the membrane tubes is controlled and the activity of oxidation catalyst is regulated, so as to ensure matching between the heating amount on the oxidation reaction side and the reaction heat required on the dehydrogenation reaction side, thereby achieving in situ heating.

The feed stock preheating temperature of the liquid phase dehydrogenation reaction ranges from 100° C. to 450° C., the temperature of the reaction ranges from 150° C. to 500° C., and the pressure ranges from 0.1 MPa to 5 MPa.

EXAMPLE 1

In the example, the preparation of camphor by liquid phase isoborneol dehydrogenation was carried out within a membrane reactor. In the example, isoborneol, as industrial grade raw material which is a solid powder at room temperature, was first dissolved in xylene to form a 30% (by mass fraction) solution having the mass reaction space velocity of 0.5 $h^{-1}$, heated by a heat exchanger up to the preheating temperature of 220° C. and then fed into the tube pass of the membrane reactor for dehydrogenation reaction. A Cu—Zn—Al catalyst (GC250 type, Japanese NGC Co., Ltd.) was filled in the tube pass, and the bed temperature of any one of dehydrogenation reaction tubes was axially measured at the arranged point using a thermowell. Oxygen was fed into the oxygen dedicated membrane tubes in the center of the tubes after passing through a flow meter. Oxygen permeated the membrane and entered the shell side for oxidation with hydrogen, with the molar ratio of oxygen to isoborneol being 1:6. A supported $Pt/Al_2O_3$ oxidation catalyst which was prepared by multiple coating-impregnating method was filled in the shell side, in which the loading mass fraction of Pt was about 1%. The pressure on the dehydrogenation reaction side was 0.6 MPa and the reaction temperatures was 220° C.; The membrane used in the reactor was a silica membrane (SMS) from Sulzer Chemtech manufacturer, and the inner diameter and outer diameter of each tube were 8 mm and 14 mm, respectively; The mixture of target product camphor and solvent xylene, on the dehydrogenation side, entered the solvent recycling section for solvent recycling, and the product camphor was transported to a finished product region.

Figure 3:
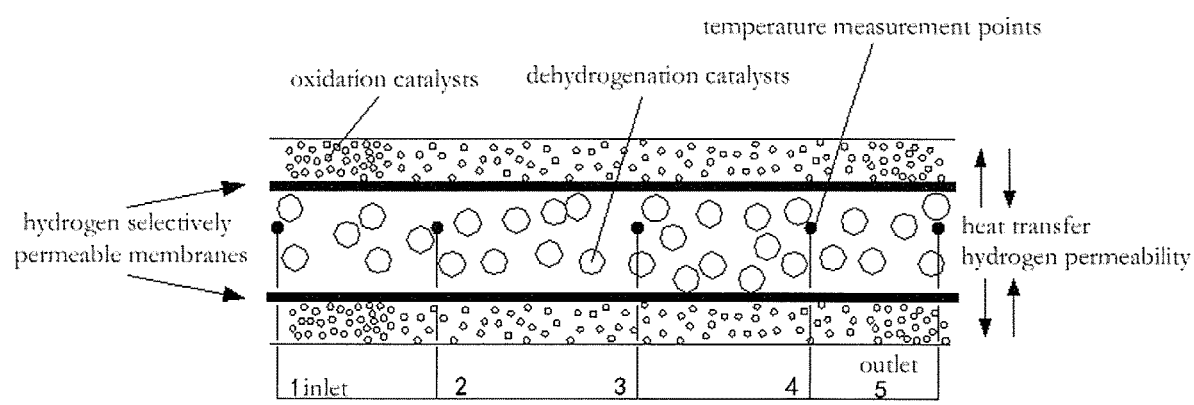
FIG. 3 is a structural schematic view of a single membrane tube in the reactor.

In the above example, the stabilized bed temperatures measured were shown in the following table (in the table, the numbers indicative of temperature measurement points were taken from FIG. 3):

| temperature measurement points | 1 (inlets) | 2 | 3 | 4 | 5 (outlets) |
|---|---|---|---|---|---|
| temperatures | 220 | 218 | 221 | 220 | 221 |

The experiment results from the above example are compared to data from other currently used processes, the results are shown in the table below:

| | catalysts | reaction temperatures/° C. | conversion rates/% | Selectivity/% |
|---|---|---|---|---|
| this example | GC250 | 220 | 99.56 | 99.78 |
| literature values* | Zn-Ca type catalysts | 295 | 99.20 | 97.00 | literature values*: taken from patent CN1027755C, Lin Yunlong, et, al., preparation of camphor by isoborneol gas phase dehydrogenation.

From the comparison results, it can be seen that isoborneol dehydrogenation reaction using the method of this application has relatively high conversion rate and selectivity, and also has more uniform bed temperature in the axial direction due to the use of multitubular structure and in situ heating system, with simple and compact devices and high production efficiency.

EXAMPLE 2

In the example, the preparation of cyclohexanone by liquid phase cyclohexanol dehydrogenation was carried out within a membrane reactor. Cyclohexanol raw material was heated by a heat exchanger up to the preheating temperature of 220° C. and then fed into the tube pass of the membrane reactor for dehydrogenation reaction. The reaction space velocity of cyclohexanol being 1.0 h$^{-1}$, and a Cu—Zn two-component catalyst DH021 (developed by Institute of Nanjing Chemicals Co., Ltd.) was filled in the tube pass, and the bed temperature of any one of dehydrogenation reaction tubes was axially measured at the arranged point using a thermowell. Oxygen was fed into the oxygen dedicated membrane tubes in the center of the tubes after passing through a flow meter, oxygen permeated the membrane and entered the shell side for oxidation with hydrogen, with the molar ratio of oxygen to cyclohexanol being 1:8. A supported Pt/Al$_2$O$_3$ oxidation catalyst which was prepared by multiple coating-impregnating method was filled on the shell side, in which the loading mass fraction of Pt was about 1%. The pressure on the dehydrogenation reaction side was 0.5 MPa and the reaction temperatures was 220° C. The membrane used in the reactor was a silica membrane (SMS) from Sulzer Chemtech manufacturer, and the inner diameter and outer diameter of each tube were 8 mm and 14 mm, respectively. The reaction product cyclohexanone was transported to a finished product region.

In this example, the temperatures measured at each point of the stabilized bed and literature values were shown in the following table (in the table, the numbers indicative of temperature measurement points were taken from FIG. 3):

| | preset values | temperature measurement points | | | | |
|---|---|---|---|---|---|---|
| | | 1 inlets | 2 | 3 | 4 | 5 outlets |
| this example/° C. | 220 | 220 | 218 | 220 | 220 | 222 |
| literature values*/° C. | 240 | 237 | 242 | 240 | 240 | 242 | literature values*: taken from the document: Stability comparison of two cyclohexanol dehydrogenation catalysts, Zhou Xiaoweng, et, al.

The experiment results from the example are compared to data from other processes currently used in industry, and the results are listed in table below:

| | catalysts | reaction temperatures/° C. | conversion rates/% | selectivity/% |
|---|---|---|---|---|
| this example | DH021 | 220 | 90.26 | 99.56 |
| literature values 1* | DH021 | 230 | 55.50 | 99.33 |
| literature values 2** | GC250 | 230 | 47.77 | 99.01 |
| literature values 3* | LYT-96 | 230 | 52.40 | 99.98 | literature values 1 and 2*: data from Nanjing DSM Dongfang Chemicals Co., Ltd.; literature values 3*: data from Hunan Yingshan Petrochemicals Plant; all from the document: Comparison of several cyclohexanol dehydrogenation catalysts, Sun Feng, et, al.

From the comparison results above, it can be seen that cyclohexanol dehydrogenation reaction using the method of this application has relatively high conversion rate and selectivity, and also has more uniform bed temperature in the axial direction due to the use of tubular structure and in situ heating system, with simple and compact devices and high production efficiency.

What is claimed is:

1. A multitubular reactor for liquid phase alcohol dehydrogenation, comprising:
   a reactor shell;
   a plurality of tubes spaced within the reactor shell, wherein the tubes are made of a gas selectively permeable membrane, which is permeable to hydrogen and oxygen but impermeable to liquid molecules, and wherein one end of the tubes is a liquid phase alcohol inlet, and another end of the tubes is a dehydrogenation product outlet, configured that a dehydrogenation reaction and an oxidation reaction take place respectively in a tube pass and a shell side of each of the tubes;
   a dehydrogenation catalyst being provided inside the tubes;
   an oxidation catalyst being provided outside the tubes and in the reactor shell;
   at least one oxygen membrane tube disposed in the reactor shell, wherein one end of the oxygen membrane tube is an oxygen inlet, and another end of the oxygen membrane tube is closed, wherein oxygen is fed from the oxygen inlet into the oxygen membrane tube directly; and
   an oxidation product outlet disposed on the reactor shell.

2. The multitubular reactor for liquid phase alcohol dehydrogenation of claim 1, wherein the gas selectively permeable membrane is made of a molecular sieve, silica, carbon, ceramics, porous stainless steel or a composite formed by two or more thereof.

3. The multitubular reactor for liquid phase alcohol dehydrogenation of claim 1, wherein the dehydrogenation catalyst is filled in the form of particles within the tubes, and the dehydrogenation catalyst comprises:
   a supported noble metal and a support thereof, wherein the noble metal is Pd, Pt, Ru or Au, and the support is a metal oxide, a molecular sieve, a carbon material or an organic polymer; and
   a non-noble metal, wherein the non-noble metal is Cu, Zn, Mn, Ni, Co, Cr or V.

4. The multitubular reactor for liquid phase alcohol dehydrogenation of claim 2, wherein the dehydrogenation catalyst is filled in the form of particles within the tubes, and the dehydrogenation catalyst comprises:
   a supported noble metal and a support thereof, wherein the noble metal is Pd, Pt, Ru or Au, and the support is a metal oxide, a molecular sieve, a carbon material or an organic polymer; and
   a non-noble metal, wherein the non-noble metal is Cu, Zn, Mn, Ni, Co, Cr or V.

5. The multitubular reactor for liquid phase alcohol dehydrogenation of claim 1, wherein the position of oxygen membrane tube is selected such that the oxidation side heating value is matched with the dehydrogenation side endothermic value at each point within the reactor.

6. The multitubular reactor for liquid phase alcohol dehydrogenation of claim 2, wherein the position of oxygen membrane tube is selected such that the oxidation side heating value is matched with the dehydrogenation side endothermic value at each point within the reactor.

7. The multitubular reactor of claim 1, wherein the oxidation catalyst is metal platinum loaded on a porous medium, and the porous medium is a metal oxide, a molecular sieve, a carbon material or hydrotalcite.

8. The multitubular reactor of claim 2, wherein the oxidation catalyst is metal platinum loaded on a porous medium, and the porous medium is a metal oxide, a molecular sieve, a carbon material or hydrotalcite.

9. A method of applying the multitubular reactor of claim 1 to the liquid phase alcohol dehydrogenation process, comprising:
   introducing a pre-heated liquid phase alcohol into the liquid phase alcohol inlet of the tubes in the reactor;
   performing a dehydrogenation reaction in the tubes;
   obtaining a dehydrogenation product from the dehydrogenation product outlet;
   feeding oxygen at a preset feed amount or feed rate into the oxygen inlet of the oxygen membrane tube in the reactor;
   permeating oxygen from the inside of the oxygen membrane tube to the inside of the reactor shell;
   performing an oxidation reaction of hydrogen with oxygen; and
   collecting water and unreacted hydrogen from the oxidation product outlet of the reactor shell.

10. The method of liquid phase alcohol dehydrogenation of claim 9, wherein the liquid phase alcohol comprises an alcohol being in liquid phase at room temperature, or an alcohol being in solid phase at room temperature and soluble in a solvent, and wherein the solvent is kept stable under the action of a dehydrogenation catalyst, and the solvent is benzene, toluene, xylene or p-cymene.

11. The method of liquid phase alcohol dehydrogenation of claim 9, wherein the temperature of the oxidation reaction is controlled to be 50-100° C. higher than that of the dehydrogenation reaction.

12. The method of liquid phase alcohol dehydrogenation of claim 9, wherein the oxygen feed amount, the oxygen feed rate or the activity of oxidation catalyst are controlled, such that the heating amount of the oxidation reaction is matched with the heat required for the dehydrogenation reaction, and the step of controlling the activity of oxidation catalyst comprises controlling the loading amount of metal platinum or doping an inert support in the catalyst.

13. The method of liquid phase alcohol dehydrogenation of claim 9, wherein the liquid phase alcohol preheating temperature of the dehydrogenation reaction ranges from 100° C. to 450° C., the temperature of the dehydrogenation reaction ranges from 150° C. to 500° C., and the pressure ranges from 0.1 MPa to 5 MPa.

14. The method of liquid phase alcohol dehydrogenation of claim 9, wherein the gas selectively permeable membrane is made of a molecular sieve, silica, carbon, ceramics, porous stainless steel or a composite formed by two or more thereof.

15. The method of liquid phase alcohol dehydrogenation of claim 9, wherein the dehydrogenation catalyst is filled in the form of particles within the tubes, and the dehydrogenation catalyst comprises:
   a supported noble metal and a support thereof, wherein the noble metal is Pd, Pt, Ru or Au, and the support is a metal oxide, a molecular sieve, a carbon material or an organic polymer; and
   a non-noble metal, wherein the non-noble metal is Cu, Zn, Mn, Ni, Co, Cr or V.

16. The method of liquid phase alcohol dehydrogenation of claim 9, wherein the position of oxygen membrane tube is selected such that the oxidation side heating value is matched with the dehydrogenation side endothermic value at each point within the reactor.

17. The method of liquid phase alcohol dehydrogenation of claim 9, wherein the oxidation catalyst is metal platinum loaded on a porous medium, and the porous medium is a metal oxide, a molecular sieve, a carbon material or hydrotalcite.

* * * * *